United States Patent [19]

Laffitte et al.

[11] 4,223,225
[45] Sep. 16, 1980

[54] TOMOGRAPHIC SYSTEM HAVING A SINGLE CASE ON WHICH ARE CARRIED THE X-RAY TUBES AND DETECTORS

[75] Inventors: Andre Laffitte; Jacques Delair, both of Paris, France

[73] Assignee: Compagnie Generale de Radiologie, Paris, France

[21] Appl. No.: 38,332

[22] Filed: May 11, 1979

[30] Foreign Application Priority Data

May 16, 1978 [FR] France .................................. 78 14406

[51] Int. Cl.² ............................................ G03B 41/16
[52] U.S. Cl. ................................... 250/445 T; 250/413
[58] Field of Search ..................... 250/445 T, 523, 413

[56] References Cited

U.S. PATENT DOCUMENTS

| | | | |
|---|---|---|---|
| 4,031,395 | 6/1977 | Le May | 250/445 T |
| 4,135,095 | 1/1979 | Watanabe | 250/445 T |

Primary Examiner—Craig E. Church
Attorney, Agent, or Firm—Roland Plottel

[57] ABSTRACT

The invention relates to a transverse axial tomographic system using a computer.

This system includes a single casing in the form of a toroid on which are carried a number of X-ray tubes that can be simultaneously or successively started very rapidly for thus irradiating a body positioned about the axis of the casing and a plurality of detectors receiving the X-rays attenuated by the body.

Such a system permits tomographic slices of organs such as the heart while they are moving.

7 Claims, 5 Drawing Figures

Fig_1
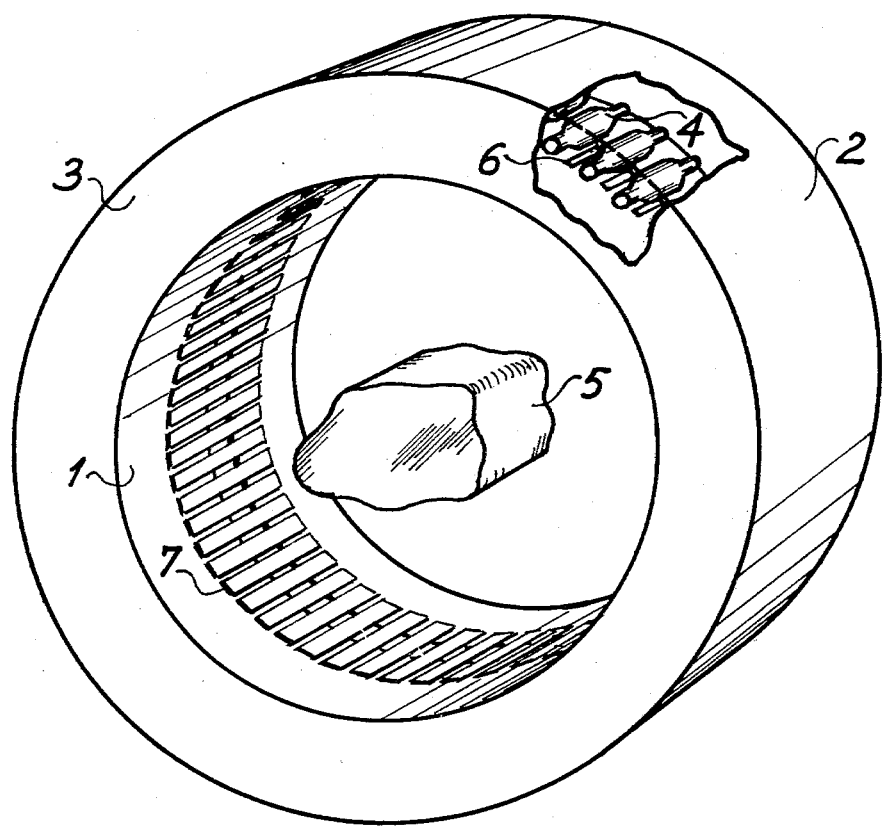

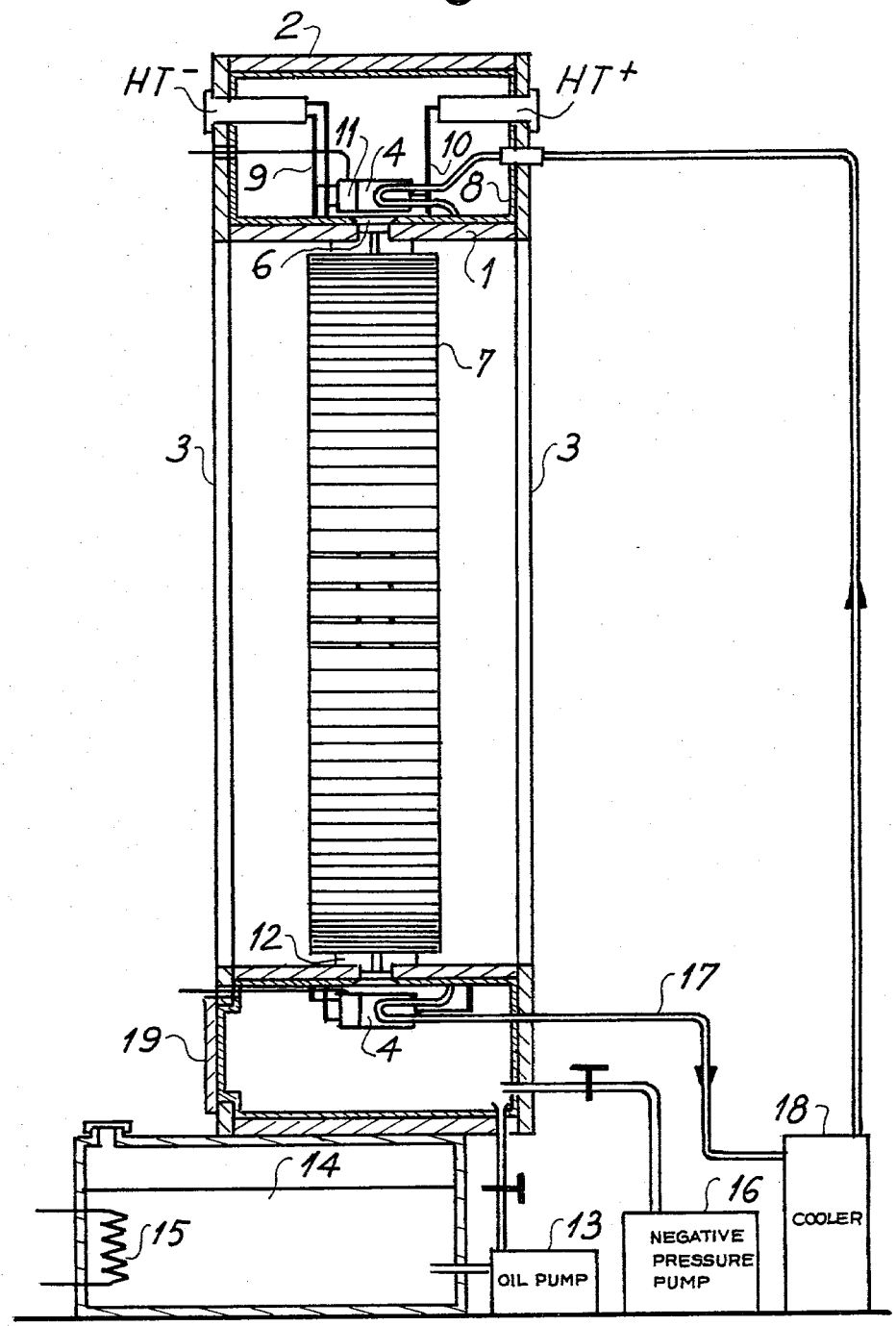

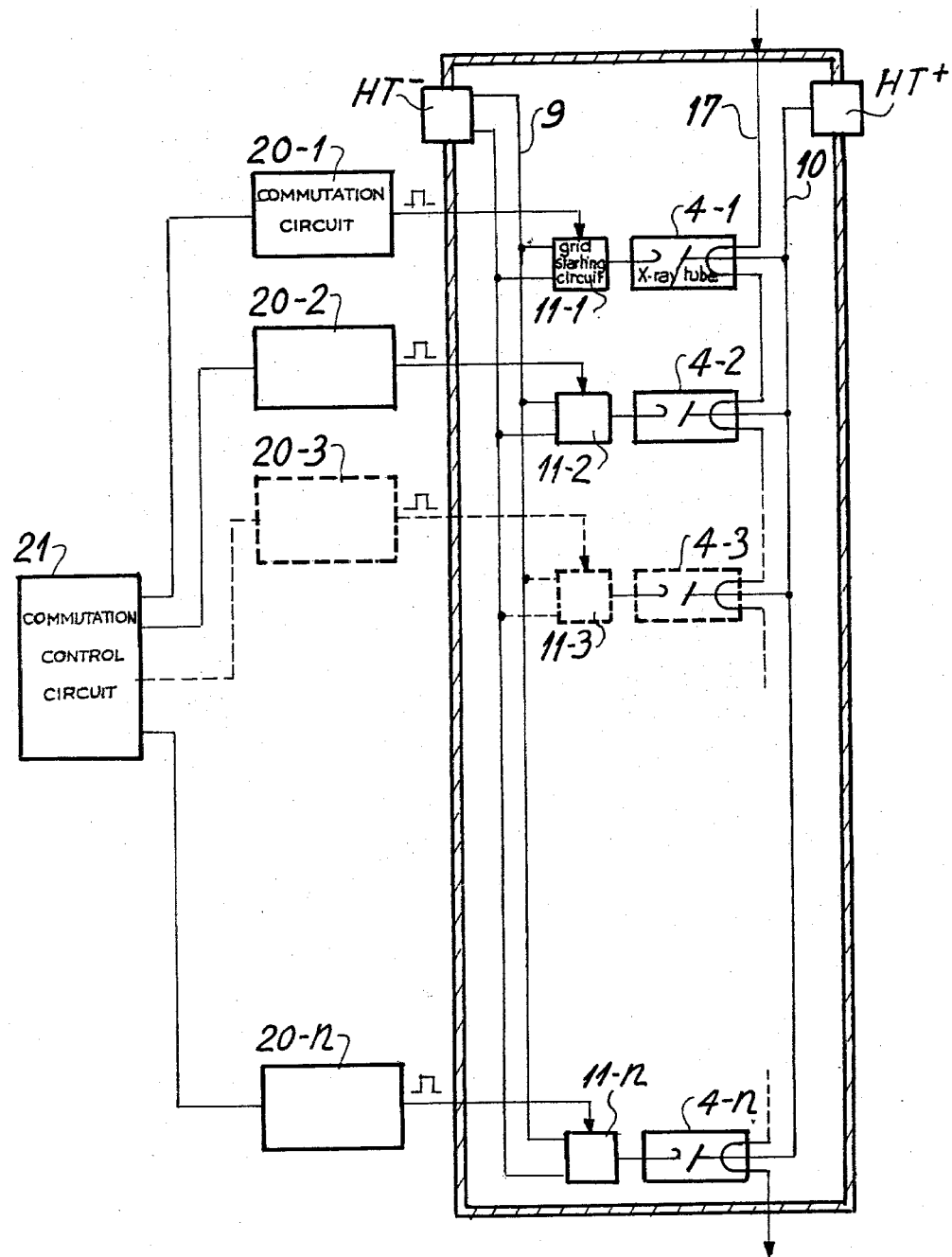

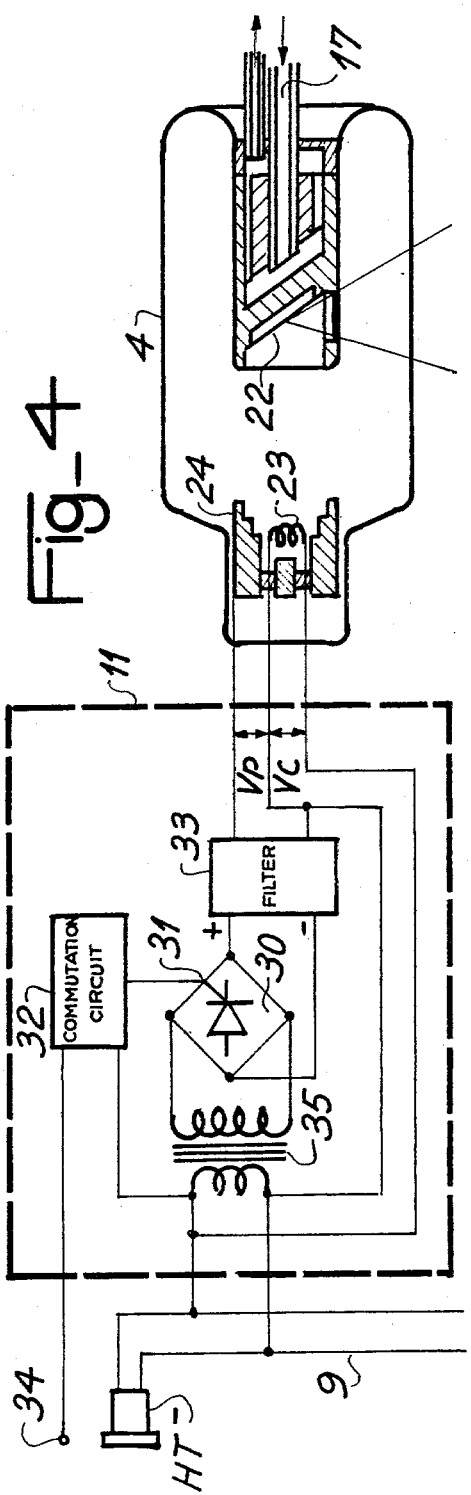
Fig_4
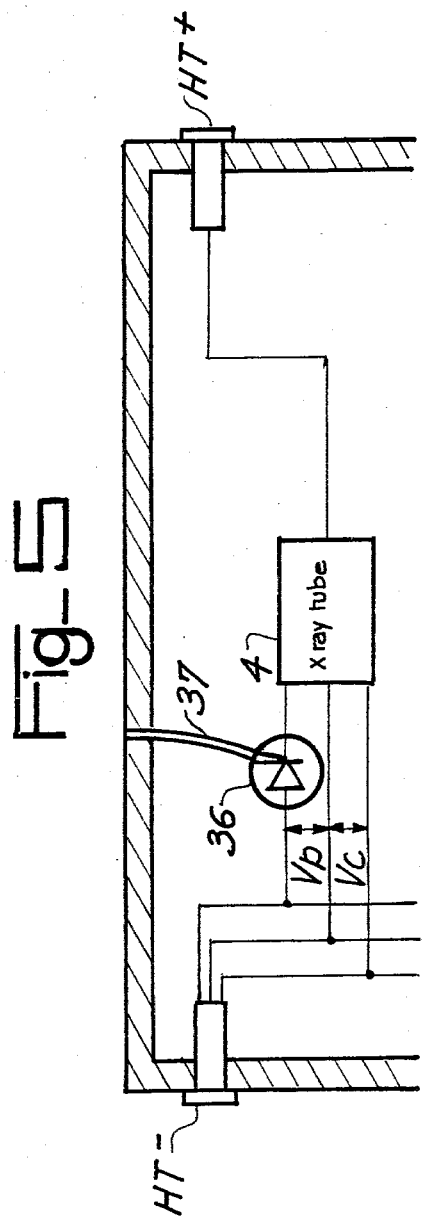
Fig_5

TOMOGRAPHIC SYSTEM HAVING A SINGLE CASE ON WHICH ARE CARRIED THE X-RAY TUBES AND DETECTORS

BACKGROUND OF THE INVENTION

1. Field of the Invention

The present invention relates to transverse axial tomographic systems using a computer and particularly to a single case on which a number of X-ray tubes and a plurality of detectors are carried.

2. Description of the Prior Art

Computerized tomographic apparatus at first included a source emitting a fine beam of X-rays in the direction of a slice of the body to be examined, and a detector positioned to receive the rays and to measure their intensity after they had passed through the body. The source-detector combination was submitted to a rectangular movement perpendicular to the direction of the beam, then to a rotation through a small angle around an axis perpendicular to the plane being examined, then again to a rectangular movement, and thus continuing until the combination had turned approximately 180°.

Such a prior art system took too long a time to produce the image of a slice of an organ in motion, such as the heart, where a time quicker than approximately 0.1 seconds is required.

To achieve faster operation, mechanical movement (translation, rotation) of the sources of X-rays and the detectors must be avoided, or at least reduced to a minimum.

In certain tomographic systems, the rectangular sweeping movements have been eliminated. The source then emits a beam of X-rays which is fan-shaped, with a large angle in the plane of the slice which transverses the body and simultaneously irradiates several detectors that are positioned one next to the other on this plane. The source-detector combination is thus only submitted to a rotational movement around the body.

In other systems, the mechanical translational movements of the source are replaced by a sweeping of the electronic beam of the X-ray tube on the target emitting the X-rays, which represents the length of translational movement.

But in all of these alternatives the time required for the tomographic picture is still long because of the mechanical rotational movement of the X-ray tube.

Several prior art patents have recognized the advantages of avoiding mechanical rotational movements. They use X-ray tubes where the tube is in the form of a toroid of very large diameter. However, the manufacture of such tubes is, in the current state of the art, very difficult and exacting.

In another patent, there is suggested the use of several tubes of the type providing a fan-shaped beam of X-rays placed successively in a circle, at the center of which is placed the body to be examined. The detectors are placed between the tubes in such a manner as to be irradiated by the tube, which is diametrically opposite. Thus, each fan-shaped beam produced by a tube irradiates the detectors placed between the two tubes which it faces.

With this arrangement, however, simultaneous irradiation of a body of normal dimensions does not include a sufficient number of directions for a tomographic slice. The opening of the fan-shaped beam of one tube is limited by the corresponding number of detectors, i.e., by the spacing between two tubes. Since this must be satisfied, the number of tubes must be small.

To remedy this drawback, it has been proposed to rotate the assembly through an angle of $2\pi/n$ ($n$=number of X-ray tubes) in small steps, in such a manner as to multiply the number of directions of measurement and of absorption. The number of tubes being small, the angle of rotation is large, and the time for acquiring the reading will be, again, too long to take a tomograph of an organ in motion. Moreover, each tube must include a protective sheath and a starting system; this arrangement appears very bulky and poorly adapted for a rotation.

The object of the invention is a tomographic apparatus having none of these inconveniences and permitting the taking of tomographic slices very rapidly.

Towards this end, the translational movement has been avoided and the rotational movement simplified and reduced to a minimum, permitting a very rapid tomograph.

According to one aspect of the invention, there is a casing in the shape of a toroid or half-toroid whose average diameter, for example, is one meter, and on which X-ray tubes are positioned one next to the other. The beams of these X-ray tubes are fan-shaped. The body to be observed is placed at the center of this toroid. The detectors cover its surface facing the body in such a manner as to measure the absorption in a very large number of directions in a given plane, more or less simultaneously (when the tubes are functioning one after the other or in groups).

According to other features of the invention, the casing may also contain grid systems for the cathodes, high-voltage starting circuits for the tubes, as well as isolated interfaces of the high voltage assuring a direct connection between a commutation circuit allowing a computer to stop or to start the tubes and a starting circuit. Thus, the bulk of the very large apparatus of high voltage isolation necessary in the apparatus having several tubes of the just-described prior art is avoided.

Other characteristics of the invention will be described in the following description, which is by way of an example that is not limiting, and illustrated in the attached Figures, in which there is shown:

BRIEF DESCRIPTION OF DRAWINGS

FIG. 1 is a perspective view, partially cut away, of a casing carrying the X-ray tubes of a tomographic apparatus according to the invention.

FIG. 2 is a partially schematic and partially sectional view through a section of a tomographic apparatus of the invention.

FIG. 3 is a schematic diagram showing the arrangement of the tubes and their control systems of a tomographic apparatus of the invention.

FIG. 4 is a schematic of an X-ray tube and its starting circuit for use in a tomographic apparatus of the invention.

FIG. 5 is a diagram of the alternative grid and control circuit for the X-ray tube of the tomographic apparatus of the invention.

DETAILED DESCRIPTION

FIG. 1 is a perspective view of a casing or case that carries several X-ray tubes of a tomographic apparatus according to the invention.

This case has an internal cylinder 1, an external cylinder 2, and two side flanges 3.

Tubes 4 are positioned next to each other in the interior space of the case in a fashion to completely surround a body 5 placed at the center, or axis, of the case.

These tubes may be, for example, tubes with fixed anodes which produce beams of X-rays that fan out with a large angle.

The internal cylinder 1 includes windows or slits 6 positioned in such a manner as to permit the X-rays provided by each tube to pass therethrough. A group of detectors 7 is placed on the cylinder's surface facing the body 5 and between the windows 6.

Each tube 4 may thus emit a beam of X-rays through a corresponding window 6, irradiate the body 5, and be collected by several detectors with an attenuation corresponding to the divergence of the beam and the absorption by the body.

The case, for example, might have a diameter of one meter, and contain a relatively large number of tubes. The number may be large, because with current technology, tubes for example with a power of up to 10 KW and having voltages up to 150 KV have only a fairly small volume (for example, a diameter of 5 cm). Thus, the angle from the axis to two adjacent tubes could be less than 10°.

In order to further increase the number of directions of measurement of the absorption, the case may be turned on its axis, in small steps or continuously through a maximum angle equal to the angle between two tubes.

The small value of this angle, and the fact that various parts are included in the single case, as will be described below with regard to FIG. 2, facilitate the tomograph's operation and a very rapid procedure.

FIG. 2 is a partially schematic partially cross-sectional view of a tomographic apparatus according to the invention.

The inside of the case, formed by the two cylinders 1 and 2 and the two side flanges 3 has a layer of lead 8 on its inner surface, with the exception of the area of the windows 6.

Also, slatted collimators 12 are positioned in front of each of the tubes, between the windows and the detectors.

All tubes 4 are fed in parallel by side busses 9 and 10. The busses 9 are connected to a high-tension connector HT-, which is mounted on the case, and deliver to the cathodes of the tubes a heating voltage for the filaments as well as a negative high tension. Bus 10 is connected to a second terminal HT+, also mounted on the case and adapted to be connected to the positive pole of the high voltage. All the tubes have their cathode inputs connected to bus 9 and the anode inputs to bus 10.

The case also includes systems for biasing the cathodes 11, circuits for starting the high voltage of the tubes, as well as interfaces insulating the high tension and for bringing about a connection between a commutation circuit and the starting circuit. These circuits are shown in detail in FIGS. 3, 4, and 5.

All of the interior of the case is filled with oil or a gas in such a manner as to electrically insulate the tubes.

When the insulation is an oil, the case is connected to an oil pump 13 and a reservoir of oil 14 which is equipped with means for heating it, such as a resistance heater 15. A negative pressure pump 16 permits drainage and rapid refilling.

The case includes openable panels 19 for maintenance access to the group of tubes and the different apparatus inside the case.

An apparatus for cooling the anodes may also be included with the case. It includes a circuit 17 permitting a circulating fluid to flow to the anodes and a cooler 18 for the fluid.

FIG. 3 schematically shows the arrangement of the tubes and the and their control circuits in the case.

N tubes, 4-1, 4-2, . . . 4-n, have their cathodes connected respectively to grid starting circuits 11-1, 11-2, . . . 11-n.

These circuits 11 are connected to bus 9 (heating voltage-negative high voltage), and to commutation circuits 20-1, 20-2, . . . 20-n. The commutation circuits are connected to a commutation control circuit 21. This permits the X-ray tubes to be started either successively, individually or in groups, or simultaneously.

The starting of each tube is directly due to the state of its starting circuit 11 which is controlled by the commutation control circuit 21.

In FIG. 3, all the X-ray tubes have their anodes connected to the bus 10, itself connected to a terminal HT+. Also, the anode cooling circuit 17 allows a cooling fluid to circulate in the anodes of all the tubes.

FIG. 4 shows in detail a typical X-ray tube and its starting circuit 11. Tube 4 has a fixed anode 22, a cathode 23, with its biasing device 24. Anode 22 is in a hollow which has the circulating cooling fluid that flows through ducts 17.

When a voltage VP, called a blocking voltage, is applied to the cathode bias 24, for example on the order of −1 KV, all emission of electrons from the cathode is blocked. When this voltage is removed, the cathode emits electrons toward the anode which in turn emits the X-rays.

Because of this, the cathode is continuously fed with a voltage VC, called the heating voltage, so that after the withdrawal of the blocking voltage electrons are emitted immediately.

Because the blocking device is connected to high voltage, and because the control can only be made by a low voltage, isolation is needed between the two.

In FIG. 4, a bridge of thyristors 30 are coupled to the high voltage through a transformer 35, while the thyristors' gates or control grids receive a control signal.

The gates 31 of the thyristors are connected to a circuit shown by block 32, that receives the control pulses, transforms them into square signals that are adapted to control the gates. The gates, blocked in the absence of a control signal, now become conducting. Thus, a voltage is now at the input terminals of filter 33, thus allowing the application of a negative voltage $V_P$, in relation to the cathode, to the biasing grid 24. This negative voltage is sufficient to block the emission of electrons from the cathode and thus there is no emission of X-rays.

A fiber optic device may also be used to transmit a signal to the starting circuit and also to assure isolation with the high voltage.

This is shown in FIG. 5, where the tube 4, whose anode is connected to HT+ and whose cathode is biased to HT−, has in its biasing circuit a device 36 for interrupting the blocking voltage, controlled by a fiber optic 37. This, for example, may be a photodiode, or again, a photoelectric cell.

For the case of this FIG. 4, the biasing voltage is only available outside of the case. It is also possible to rearrange it as in FIG. 4. In FIG. 4, the bias potential is available at the output of filter 33, which is in the interior of the case.

By successively starting the tubes, the body is irradiated along its entire slice in a very large number of directions by a beam fan-shaped with a wide opening. This number of directions may be also increased by turning the case either in small steps or continuously through an angle equal to the angle from the center to two adjacent tubes, which, according to the invention, is a very small one.

The X-ray here, attenuated by the body, is received by the detectors positioned on the case carrying the X-ray tubes. These detectors are placed side by side between the windows, thus permitting passage of the X-rays from the several tubes.

The tomographic system according to the invention, joined to a computer, permits viewing in layers of parts of the body having organs in movement—the heart, for example.

We claim:

1. A transverse axial tomographic apparatus comprising a hollow case formed by inner and outer concentric cylinders joined by two side flanges and adapted to straddle a body whose tomograph is to be taken, said inner cylinder having windows for the passage of X-rays therethrough; a plurality of X-ray tubes and associated collimators positioned one next to another inside said case, in a circle around the body for irradiating the body and positioned in relation to said windows for the passage of their X-ray beams therethrough; a system for starting the tubes' cathodes; a plurality of detectors mounted on the external surface of the inner cylinder except over said windows, and diametrically opposite the plurality of tubes for receiving the X-ray beams after they have passed through the body; a lead lining on the interior of said case, except in the region of said windows; and a dielectric fluid filling said case.

2. A tomographic apparatus according to claim 1 wherein the X-ray tubes have a cathode control grid and a fixed-surface anode inclined for producing with the collimators an X-ray beam which is flat and fan-shaped with a wide fan-out angle.

3. A tomographic apparatus according to claim 1 or claim 2, further comprising inside the case common high-voltage busses for feeding the tubes, the starting system, and a unitary circuit for cooling the anodes with oil.

4. A tomographic apparatus according to claims 1 or 2 wherein the system for starting the cathode is included in the case and is adapted to be connected to a high-voltage source needed for controlling the cathodes; commutation circuits connected to, and electrically isolated from the high voltage for controlling said starting systems, a control circuit for controlling said commutation circuits for very rapid and selective starting of the tubes.

5. A tomographic apparatus according to claim 4 wherein said high voltage isolation includes a fiber optic connection.

6. A tomographic apparatus according to claims 1 or 2 characterized in that the case is rotatably mounted on its axis for movement during a tomograph a distance equal to the distance between two tubes.

7. An apparatus for use in a computer-driven transverse axial tomographic system comprising a hollow annular-shaped case adapted to be positioned around a body whose tomograph is to be taken, comprising a plurality of X-ray tubes positioned inside said case one next to the other and for directing their X-ray beams through windows in the case wall toward the body;
a plurality of circuits mounted inside said case for starting each of said X-ray tubes;
a plurality of X-ray detectors positioned on the case between the windows opposite the plurality of tubes for receiving the X-ray beams after they have passed through the body;
and commutation means for controlling the starting circuits and thus of said X-ray tubes.

* * * * *